(12) United States Patent
Zhang (10) Patent No.: US 10,049,128 B1
(45) Date of Patent: Aug. 14, 2018

(54) OUTLIER DETECTION IN DATABASES

(71) Applicant: Symantec Corporation, Mountain View, CA (US)

(72) Inventor: Yuting Zhang, Sichuan (CN)

(73) Assignee: Symantec Corporation, Mountain View, CA (US)

(*) Notice: Subject to any disclaimer, the term of this patent is extended or adjusted under 35 U.S.C. 154(b) by 348 days.

(21) Appl. No.: 14/588,054

(22) Filed: Dec. 31, 2014

(51) Int. Cl.
*G06F 17/30* (2006.01)
*G06F 19/00* (2018.01)

(52) U.S. Cl.
CPC .. *G06F 17/30371* (2013.01); *G06F 17/30289* (2013.01); *G06F 19/704* (2013.01)

(58) Field of Classification Search
CPC ............... G06F 19/12–19/16; G06F 19/704
USPC ................................ 707/692, 737, 758, 803
See application file for complete search history.

(56) References Cited

U.S. PATENT DOCUMENTS

| | | | | |
|---|---|---|---|---|
| 5,918,238 A * | 6/1999 | Hayashi | ................ | G06F 17/211 345/440 |
| 8,774,504 B1 * | 7/2014 | Sundareswara | .... | G06K 9/00201 382/165 |
| 2002/0002414 A1 * | 1/2002 | Hsiung | .................. | G05B 15/02 700/95 |
| 2003/0078703 A1 * | 4/2003 | Potts | .................. | G01N 15/1456 701/1 |
| 2003/0078738 A1 * | 4/2003 | Wouters | ................ | G06F 19/363 702/22 |
| 2004/0117164 A1 * | 6/2004 | Elling | ................... | G06F 19/707 703/11 |
| 2004/0249779 A1 * | 12/2004 | Nauck | ................ | G05B 13/0275 706/47 |
| 2005/0005261 A1 * | 1/2005 | Severin | .................... | G06F 8/316 717/108 |
| 2008/0167837 A1 * | 7/2008 | Basak | ................ | G06K 9/00503 702/179 |
| 2008/0234977 A1 * | 9/2008 | Aggarwal | ............ | G06K 9/6284 702/179 |
| 2009/0132347 A1 * | 5/2009 | Anderson | .............. | G06Q 30/02 705/14.52 |
| 2010/0007738 A1 * | 1/2010 | Lehnert | .................. | H04N 7/181 348/159 |

(Continued)

OTHER PUBLICATIONS

Cui, Hongyin, "Online Outlier Detection over Data Streams," 2005, 63 pages.

(Continued)

*Primary Examiner* — Hanh B Thai
(74) *Attorney, Agent, or Firm* — Patent Law Works LLP (57) ABSTRACT

Various systems, methods, and processes for identifying outliers in a data set stored in a database are disclosed. A subset of data is extracted from a data set. Data descriptors are allocated to the subset of data. A model of the subset of data is created based on attributes of the data descriptors. An iteration of an outlier detection process based on the model is then executed. The outlier detection process evaluates the subset of data, and the outlier detection process evaluates the data set based on the results of the evaluation of the subset of data. The outlier detection process, which can implement and/or use a Random Sample Consensus (RANSAC) algorithm, identifies outliers in the data set stored in the database.

15 Claims, 9 Drawing Sheets

(56) References Cited

U.S. PATENT DOCUMENTS

| | | | | |
|---|---|---|---|---|
| 2010/0280847 | A1* | 11/2010 | Schaffer | G06Q 50/24 705/3 |
| 2012/0011119 | A1* | 1/2012 | Baheti | G06F 17/30247 707/737 |
| 2014/0279727 | A1* | 9/2014 | Baraniuk | G06N 99/005 706/11 |
| 2015/0095360 | A1* | 4/2015 | Vrcelj | G06F 17/30061 707/758 |
| 2015/0134315 | A1* | 5/2015 | Sarmiento | G06F 19/16 703/11 |
| 2015/0248586 | A1* | 9/2015 | Gaidon | G06K 9/00711 382/103 |
| 2015/0370781 | A1* | 12/2015 | Galle | G06F 17/271 704/9 |

OTHER PUBLICATIONS

Franklin, Sarah et al., "Robust Multivariate Outlier Detection Using Mahalanobis' Distance and Modified Stahel-Donoho Estimators," 1992, pp. 697-730.

Gomez, Lluis et al., "MSER-Based Real-Time Text Detection and Tracking," 2014 International Conference on Pattern Recognition, 2014, 6 pages.

Guthrie, David, "Unsupervised Detection of Anomalous Text," Jul. 2008, Department of Computer Science, University of Sheffield, 186 pages.

Hodge, Victoria et al., "A Survey of Outlier Detection Methodologies," Artificial Intelligence Review, 2004, pp. 85-126, vol. 22(2).

Kriegel, Hans-Peter et al., "Outlier Detection Techniques," The 2010 SIAM International Conference on Data Mining, 2010, 73 pages.

Liu, Xutong, "Spatial Outlier Detection: Random Walk Based Approaches," Nov. 2, 2010, 10 pages.

Loureiro, Antonio et al., "Outlier Detection Using Clustering Methods: a data cleaning application," 2004, 12 pages.

Moonesinghe, H.D.K. et al., "OutRank: A Graph-Based Outlier Detection Framework Using Random Walk," International Journal on Artificial Intelligence Tools, vol. XX, No. X (2007), 18 pages.

Phua, Clifton et al., "A Comprehensive Survey of Data Mining-based Fraud Detection Research," 2010, 14 pages.

Raguram, Rahul et al., "A Comparative Analysis of RANSAC Techniques Leading to Adaptive Real-Time Random Sample Consensus," Springer-Verlag Berlin Heidelberg, 2008, pp. 500-513.

Seo, Songwon, "A Review and Comparison of Methods for Detecting Outliers in Univariate Data Sets," 2006, University of Pittsburgh, 59 pages.

* cited by examiner

OUTLIER DETECTION IN DATABASES

BACKGROUND OF THE INVENTION

Field of the Invention

This invention relates to data analysis and, more particularly, to outlier detection in databases.

Description of the Related Art

Many companies and organizations implement databases to manage their data. Such databases can often times store voluminous amounts of data. The data stored in a large database can be shared, used, modified, and/or updated by multiple users of the database. For example, different teams in a company can use data stored in a shared database to perform data analysis, modify, rewrite, and/or merge the shared data. Such actions, if performed repeatedly, can result in a reduction in data quality of the data stored in the database. Therefore, over time, "dirty" data can exist in the database.

Examples of "dirty" data in a database that can result in a reduction in data quality include, but are not limited to, duplicate entries, erroneous data, bad address information, data about customers and/or employees that is not updated, etc. Therefore, if multiple users constantly move data in and out of a database, maintaining an up to date master (or clean) copy of the data can be challenging.

Typically, data analysis to identify such "dirty" data requires prior knowledge and/or information about the target object stored in the database. For example, information such as the Internet Protocol (IP) address of the user performing changes to the data, the expiration date of data, etc. are required to identify "dirty" data. Moreover, prior knowledge of the data is also required if the data stored in the database is in a format that is not easily recognized by a database administrator (e.g., data in string, integer, or bytea formats).

SUMMARY OF THE INVENTION

Various systems, methods, and processes for identifying outliers in a data set stored in a database are disclosed. For example, one method involves extracting a subset of data from a data set. In this example, the data is a string. The method allocates data descriptors to the subset of data that describe the subset of data. The method then creates a model of the subset of data based on attributes of the data descriptors.

In one embodiment, the method executes an iteration of an outlier detection process based on the model. In this example, the outlier detection process performs at least two steps. First, the outlier detection process evaluates the subset of data, and second, the outlier detection process evaluates the data set based on the results of the evaluation of the subset of data. By doing so, the outlier detection process identifies outliers in the data set. In some embodiments, the outlier detection process is a Random Sample Consensus (RANSAC) algorithm.

In other embodiments, a clustering process is used to identify a filtering threshold of the subset of data based the model of the subset of data. The method then filters the data set based on the filtering threshold of the subset of data. The method then executes another iteration of the outlier detection process. Executing another iteration creates another model of the subset of data, and identifies a similarity threshold of the another subset of data based on the another model. In this example, the another subset of data is part of the data set.

In some embodiments, the method identifies outliers in the data set by comparing the model of the subset of data and the another model of the another subset of data. The method then filters the data set using a model with the higher similarity threshold.

In one embodiment, the data set is part of a database application. Identifying the outliers in the data set detects dirty data in the data set that is part of the database application. In some embodiments, the set of data descriptors describe a length, a character set, a co-occurrence, a frequency, an entropy, a similarity, or a segmentation of the subset of data.

In other embodiments, using the clustering process creates a fingerprint that associates the subset of data and the data set based on the data descriptors. In this example, the method determines a value distribution of the set of data descriptors based on the fingerprint created using the clustering process, and calculates the similarity between the subset of data and the data set based on the value distribution.

BRIEF DESCRIPTION OF THE DRAWINGS

The present invention may be better understood, and its numerous objects, features and advantages made apparent to those skilled in the art by referencing the accompanying drawings.

While the invention is susceptible to various modifications and alternative forms, specific embodiments of the invention are provided as examples in the drawings and detailed description. It should be understood that the drawings and detailed description are not intended to limit the invention to the particular form disclosed. Instead, the intention is to cover all modifications, equivalents and alternatives falling within the spirit and scope of the invention as defined by the appended claims.

DETAILED DESCRIPTION

Introduction

Figure 1:
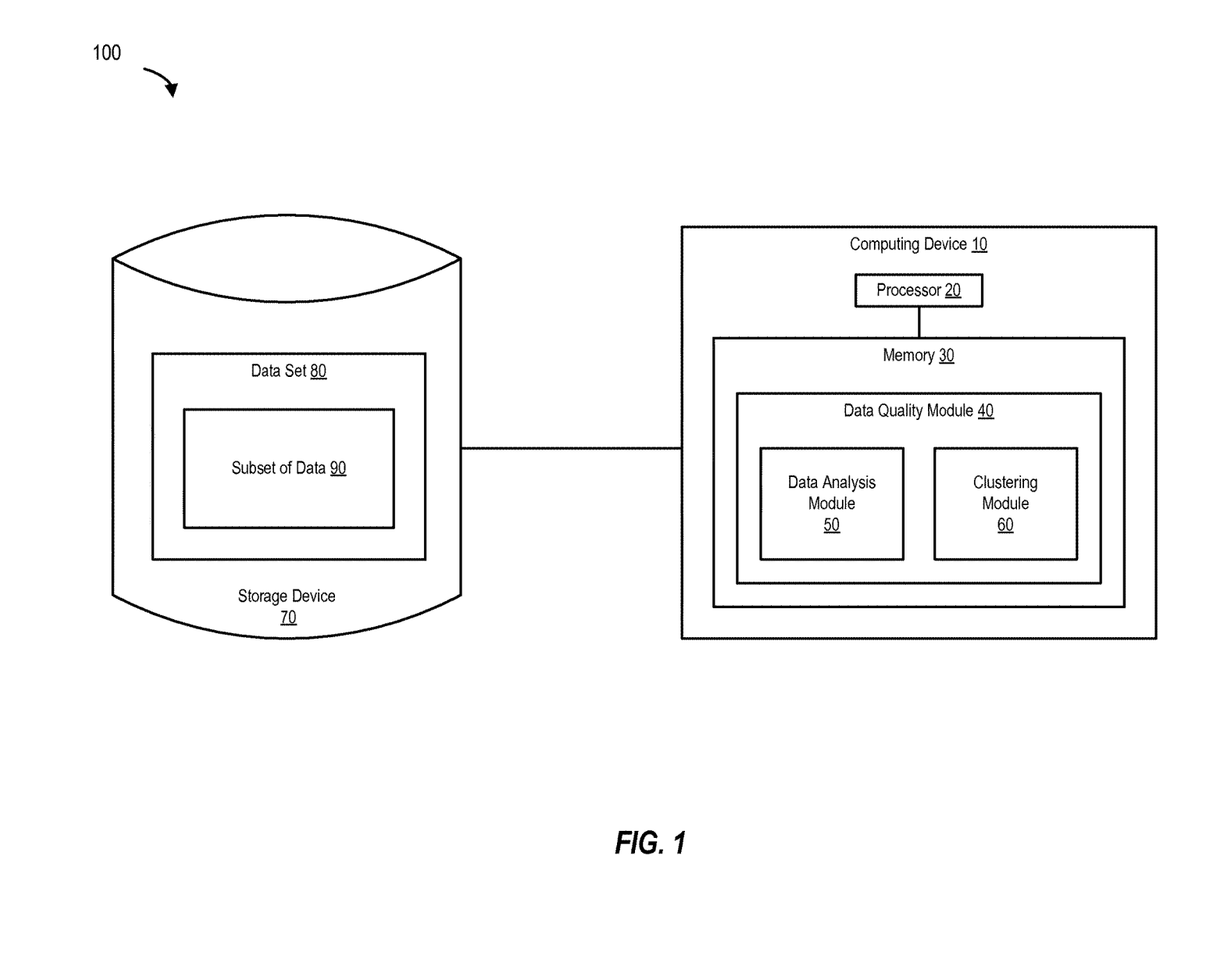
FIG. 1 is a block diagram of a system for performing data analysis, according to one embodiment of the present invention.

FIG. 1 is a block diagram of a system for performing data analysis. This system includes a computing device 10 and a storage device 70. As shown, computing device 10 is coupled to storage device 70. Computing device 10 can be any of a variety of different types of computing devices, including a server, personal computing device, laptop computer, net book, personal digital assistant, cellular phone, or the like.

Computing device 10 includes a processor 20, and memory 30. Computing device 10 also includes a data quality module 40 which implements a data analysis module 50 and a clustering module 60. Storage device 70 stores a data set 80 which includes a subset of data 90. It is noted that this is a simplified example, and that other embodiments can include far more complex organizational and configuration schemes than are shown here.

Computing device 10 is coupled to storage device 70. In this example, storage device 70 stores data set 80, but can also store data in other formats (not shown). Storage device 70 can be a persistent storage device and can include one or more of a variety of different storage devices, including hard disks, compact discs, digital versatile discs, solid state drive (SSD) memory such as flash memory, and the like, or one or more logical storage devices such as volumes implemented on one or more such physical storage devices.

Computing device 10 and storage device 70 can be integrated (e.g., where the storage device is coupled to the node's internal processing devices by an internal bus and is built within the same chassis as the rest of the node) or separate. If separate, computing device 10 and storage device 70 can be coupled by a local connection (e.g., using a technology such as Bluetooth™, Peripheral Component Interconnect (PCI), Small Computer System Interface (SCSI), or the like) or via one or more networks such as the Internet or a storage area network. Computing device 10 can be a client device or client system (as shown in FIG. 2) and can be used to perform outlier detection in data sets stored in a database.

Figure 2:
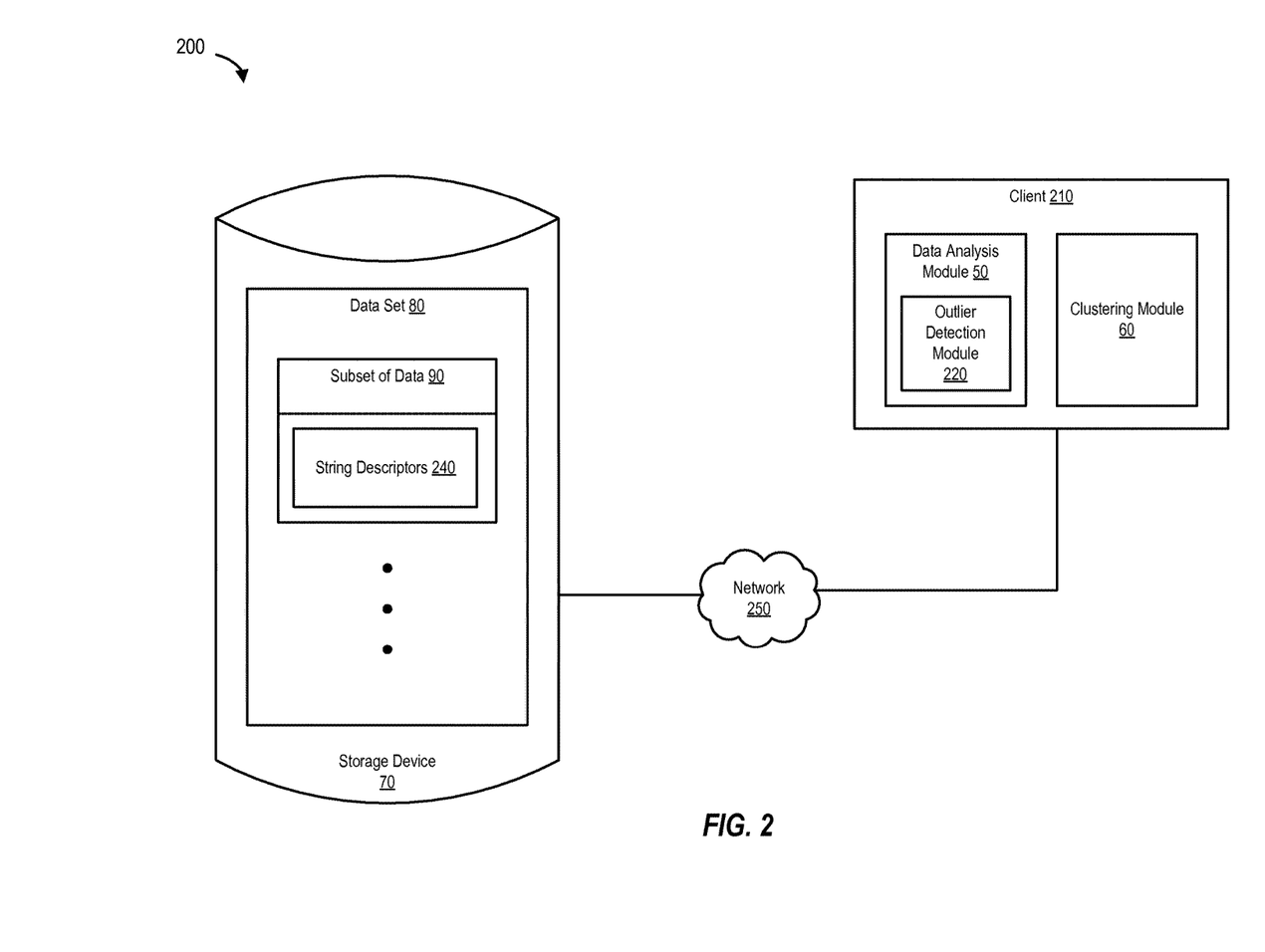
FIG. 2 is a block diagram of a system for evaluating data based on an outlier detecting algorithm, according to one embodiment of the present invention.

FIG. 2 is a block diagram of a system for evaluating data based on an outlier detection process. As shown in FIG. 2, storage device 70 can be coupled to a client 210 via network 250. Data set 80 on storage device 70 includes subset of data 90. String descriptors 240 are allocated to subset of data 90. In this example, string descriptors 240 describe subset of data 90. Client 210 includes data analysis module 50 and clustering module 60. Data analysis module 50 implements an outlier detection module 220. Outlier detection module 220 uses, or can implement, an outlier detection algorithm. Clustering module 60 uses, or can implement, a clustering algorithm.

Data descriptors, when used in conjunction with an iterative outlier detection algorithm such as the Random Sample Consensus (RANSAC) algorithm can be useful for performing automatic outlier detection in data sets stored in a database. Data descriptors and their use with the RANSAC algorithm is discussed below.

Data Descriptors

As noted above, identifying outliers in a data set stored in a database can be useful to maintain the data quality in the database. However, outlier detection can be challenging when the data stored in the database is in a text format, a string format, an integer format, or in a bytea format because the outliers in a data set that contains data in the aforementioned formats can be difficult to identify without prior knowledge of the target object. Therefore, a data set with string data, integer data, or bytea data has to be modeled based on data descriptors before it can be implemented for use with an outlier detection process.

In one embodiment, string descriptors, which are data descriptors used to describe string data (or simply a string), can be used in conjunction with an outlier detection algorithm to perform outlier detection. For example, string descriptors can describe a length, a character set, a co-occurrence, a frequency, an entropy, a similarity, or a segmentation of subset of data 90. In this example, the aforementioned attributes of the string descriptors can be used to create a model of subset of data 90. In some embodiments, this model can then be used by an outlier detection algorithm such as the Random Sample Consensus (RANSAC) algorithm to identify outliers in data set 80.

In some embodiments, several features (or attributes) of string data are used to create a model that describes the string data. As noted above, these features or attributes can include a length, a character set, a co-occurrence, a frequency, an entropy, a similarity, or a segmentation of the data set (or a subset of data of the data set). In this example, in a length histogram, the length of string data can be represented on the X-axis, and the Y-axis can represent the number of strings. In an alternate example, different strings can contain different characters. Data sets with different usages can also contain different character sets. Therefore, the model can use character sets to describe the character attributes of the string(s) (e.g., by using an Unicode character table).

The frequency attribute describes the number of times a character appears in a string. For example, if a string is 'aba,' the character changes two times, so the frequency attribute of the string is 2/2, which is equal to 1. Similarly, if the string is 'abbbb,' the character changes once, so the frequency attribute of the string is 1. In some embodiments, these frequency attributes can be represented on the X-axis as the frequency value, and the Y-axis can represent the number of strings in a frequency histogram.

Entropy refers to the unpredictability of the contents of a data set. In the model, the X-axis represents the string length, and the Y-axis represents the string entropy multiplied by the string length. In an alternate example, the X-axis can represent the string entropy and the Y-axis can represent the number of strings. In one embodiment, the entropy-based attributes can be represented by an entropy histogram to be used in creating a model for evaluation (e.g., an outlier detection process and/or algorithm).

In other embodiments, co-occurrence of an element of string data can also be used to create the model. For example, if two string elements appear together in the data set, a co-occurrence can be declared and the model can group those string elements together to be used in creating the model. In alternate embodiments, some strings can be segmented by one or more symbols. For example, a string can be segmented based on a package name (e.g., segmentation histogram of package_name of data set 80), Uniform Resource Locator (URL), and/or an IP address. In this example, the X-axis represents the number of segments and the Y-axis represents the number of strings in a segmentation histogram.

In some embodiments, a similarity attribute can be used to model subset of data 90 (in addition to one or more attributes). For example, one string may look like another string, and these strings may have a common subsequence. In this example, a longest common subsequence (LCS) can be used to describe the similarity attribute of the string(s) (e.g., to find the longest subsequence common to all sequences in a set of sequences).

Therefore, in this matter, features or attributes of string data can be used to describe the string data for the purpose of creating an evaluation model. To create the integrated model for evaluation by the outlier detection process, all available attributes are extracted from the string data, and the value of the attributes can be used to calculate the difference between two or more sets (or subsets) of data.

Figure 3:
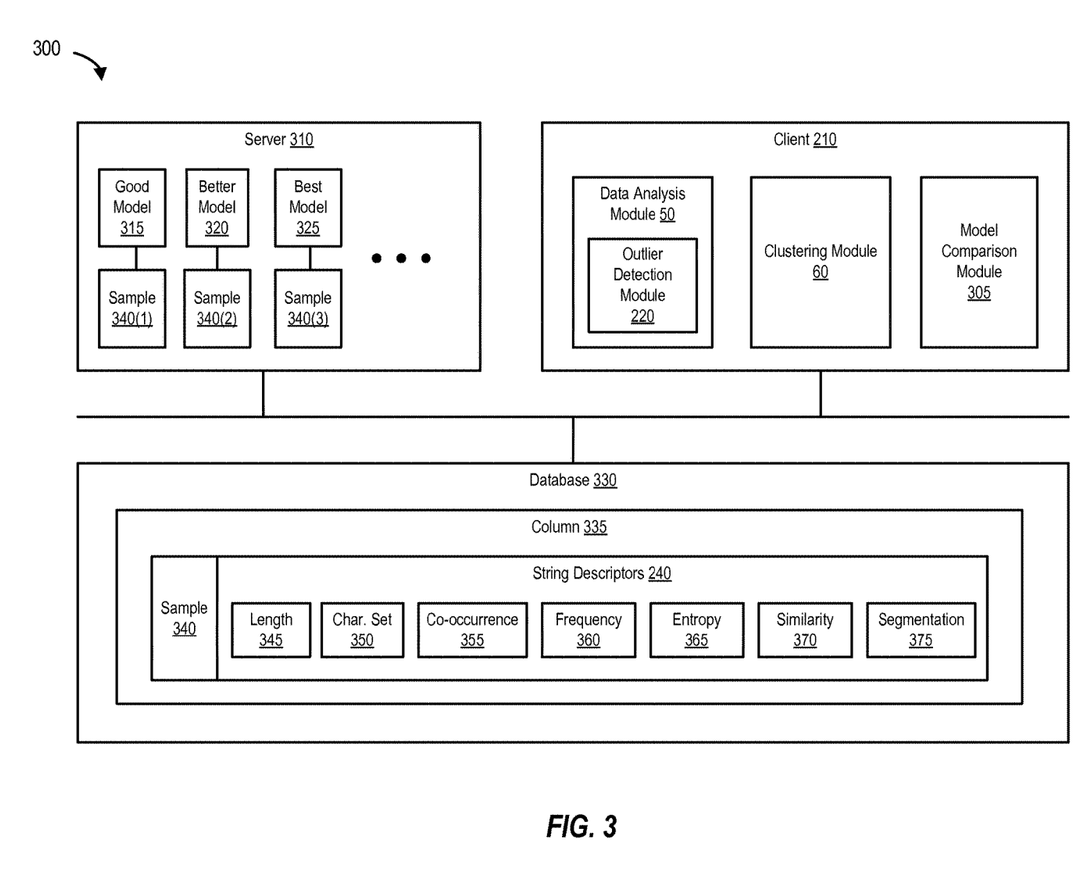
FIG. 3 is a block diagram of a system for allocating string descriptors, according to one embodiment of the present invention.

FIG. 3 is a block diagram of a system for allocating string descriptors. Client 210 is a computing device that contains data analysis module 50, clustering module 60, and model comparison module 305. Data analysis module 50 implements outlier detection module 220. Client 210 is coupled to database 330 which contains column 335 (in addition to several additional columns which are not shown in FIG. 3). Sample 340 is a data sample (e.g., subset of data 90) taken from column 335. String descriptors 240 are allocated to sample 340. As shown in FIG. 3, the attributes or features of string descriptors 240 include length 345, character set 350, co-occurrence 355, frequency 360, entropy 365, similarity 370, and segmentation 375. It is noted that this is a simplified example, and that other embodiments can include additional data descriptors than are shown here.

As shown in FIG. 3, server 310 is coupled to client 210 and database 330. Server 310 stores several models for comparison (e.g., by model comparison module 305). For example, server 310 stores good model 315 associated with sample 340(1), better model 320 associated with sample 340(2), and best model 325 associated with sample 340(3).

In one embodiment, column 335 is extracted from database 330 and sample 340 is extracted from column 335. String descriptors 240 are allocated to sample 340. The data distribution (or value distribution) of the features of the string descriptors (e.g., length 345, character set 350, co-occurrence 355, frequency 360, entropy 365, similarity 370, and segmentation 375) is calculated using a clustering algorithm/process.

In other embodiments, data processed by a clustering algorithm (e.g., the attributes of string descriptors 240) can be used to create a fingerprint. Each fingerprint has a fingerprint circle which represents a cluster edge, and the distance between fingerprint circles represent the amount of a class. Fingerprints present the data distribution feature (e.g., based on features and/or attributes of the data descriptors) and can be used to perform similarity comparison between data sets. In this example, the values of one feature (e.g., length or entropy) are calculated for sample 340. A clustering process can then be used to divide the calculated values into two classes (e.g., using the Otsu's method) to determine a classification number (e.g., best_classification_number). The classification process is executed again based on the classification number.

In some embodiments, to compare two (or more) models which are produced from the subset of data and the data set, the clustering algorithm can also be used to cluster the data distribution of the attributes/features produced by the data descriptors to calculate the difference between the models. A high level of similarity between two models can be given a high score (e.g., a similarity score). As discussed below, executing a second or subsequent iteration of an outlier detection algorithm can create another model of the subset of data and can identify another threshold and thus, another similarity score of another subset of data based on another model. As noted above, upon comparison of the distribution of the attributes/features produced by the data descriptors (also called a fingerprint), a similarity score is produced. Similarity scores between two or more models can be compared, and the model with the higher similarly score can be filtered using a similarity threshold.

Some embodiments provide for at least two types of thresholds. The first type of threshold is a similarity threshold (discussed above), which is a threshold for a similarity score and can be used to stop or continue an interation of an outlier detection algorithm. The second type of threshold is a filtering threshold, which is a threshold for data filtering, and is created by the clustering algorithm. As discussed above, the clustering algorithm can be used to determine the threshold (e.g., an edge represented by the filtering threshold) of outliers, and can create fingerprints to compare different models because different sets of data distribution results will result in different clustering results. In other embodiments, an iteration of an outlier detection algorithm can be stopped if the similarity score meets (or exceeds) the similarity threshold. The clustering algorithm can then use the features/attributes of the data descriptors of the model and determine the cluster edge (e.g., the filtering threshold) to filter the data set.

In an alternate embodiment, the values of all features (or attributes) of the string descriptors allocated to sample 340 is separately calculated using a clustering algorithm or process. This results in at least seven fingerprints (e.g., based on the seven attributes of string descriptors 240—length 345, character set 350, co-occurrence 355, frequency 360, entropy 365, similarity 370, and segmentation 375). The seven fingerprints can represent sample 340 in a three-dimensional space and can be used to create a first model (e.g., good model 315 associated with sample 340(1)). Good model 315 can then evaluated using an outlier detection process (e.g., the RANSAC algorithm) to determine whether other models are necessary (e.g., better model 320 associated with sample 340(2), and best model 325 associated with sample 340(3), etc.) for evaluation to identify an optimum number of outliers in the data set (e.g., based on a predetermined threshold).

Data Analysis Using RANSAC

The RANSAC algorithm, which is an example of outlier detection algorithm and/or process, can be executed based on the models described above. The RANSAC algorithm is an iterative algorithm which is used, in some embodiments, to estimate parameters of the created models (e.g., good model 315, better model 320, best model 325, etc.) from a set of observed data (e.g., samples 380(1)-(3) associated with good model 315, better model 320, and best model 325 respectively). Because the RANSAC algorithm is a non-deterministic algorithm (e.g., the algorithm only produces results with a certain probability), multiple iterations of the RANSAC algorithm can be executed to increase the probability of detecting the optimum number of outliers in a data set (e.g., based on a similarity threshold).

The following is an example of the RANSAC algorithm, when the algorithm is applied to detecting outliers in a database based on data descriptors:

```
best_model=None
best_value=0
   extract sample of data
   model=fit model with Data Descriptor
   value=evaluate the model with another sample (another
      model)
   if value>best_value:
      value=best_value
      best_model=model
```

Figure 4:
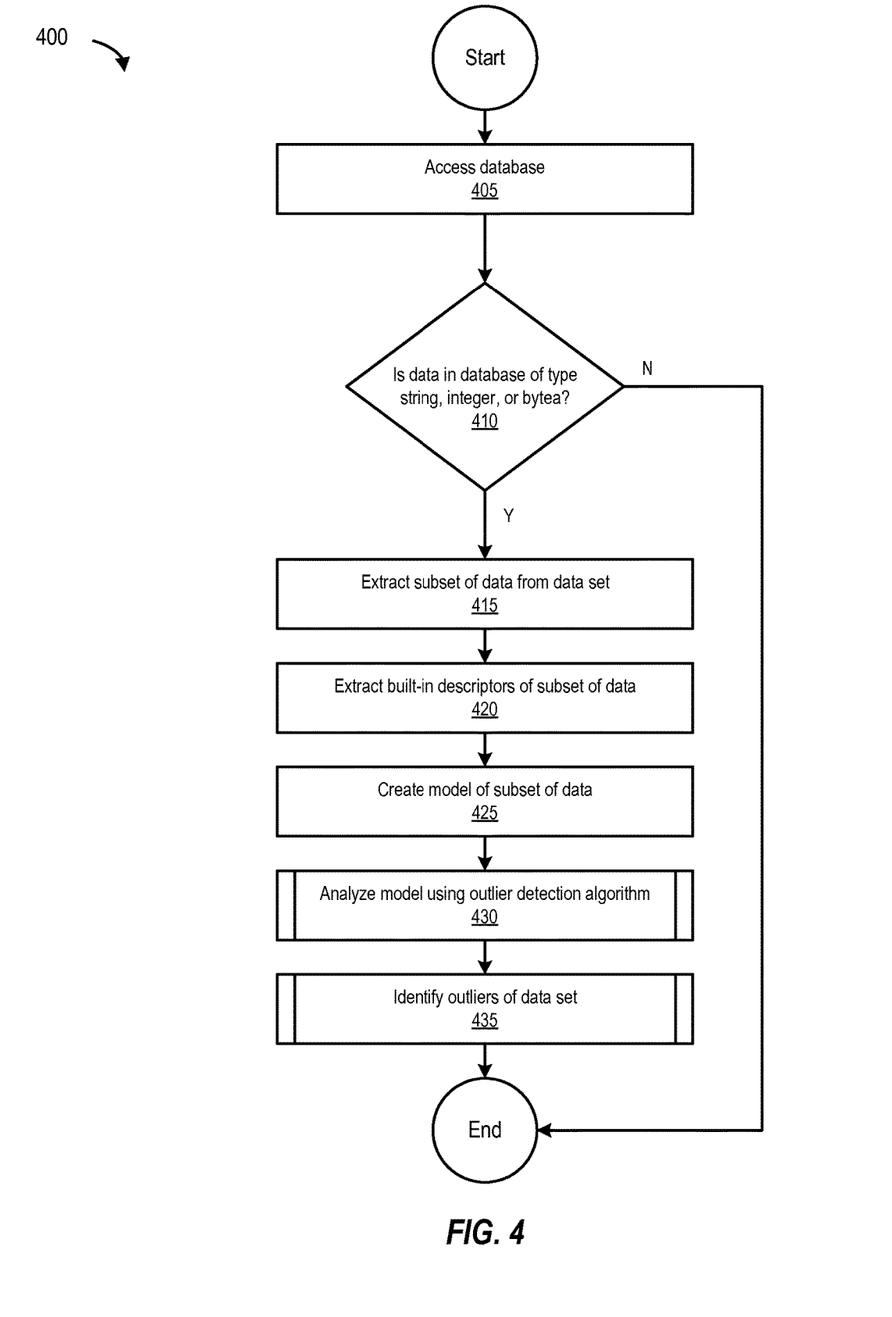
FIG. 4 is a flowchart that illustrates a process for identifying outliers in a data set based on an outlier detecting algorithm, according to one embodiment of the present invention.

FIG. 4 is a flowchart that illustrates a process for identifying outliers in a data set. The process begins at 405 by accessing a database (e.g., database 330). At 410, the process determines if the data (e.g., data set 80) in database 330 is string data, integer data, or bytea data. If the data in database 330 is not string data, integer data, or bytea data (e.g., if the data is image point data), the process ends. However, if the data in database 330 is string data, integer data, or bytea data, the process, at 415, extracts a subset of data (e.g., subset of data 90) from a data set stored on database 330 (e.g., data set 80). At 420, the process extracts built-in descriptors (e.g., string descriptors 240) of the subset of data. At 425, the process creates a model (also called first or evaluation model) of the subset of data based on the attributes of the extracted built-in descriptors (e.g., good model 315 as shown in FIG. 3).

At 430, the process analyzes the model based on an outlier detection algorithm (e.g., an outlier detection process based on the RANSAC algorithm). If the process analyzes the model based on the RANSAC algorithm, an iteration of the RANSAC algorithm performs a two-step process. First, the iteration of the RANSAC algorithm evaluates the subset of data (e.g., sample 340(1)) based on the good model 315). Second, the same iteration of RANSAC algorithm evaluates the entire data set (e.g., data set 80) based on the results of evaluating the subset of data. The process ends at 435 by identifying outliers in the data set.

As noted above, after an iteration of the RANSAC algorithm is complete, a model (e.g., good model 315 based on sample 340(1)) can be evaluated to determine whether the model identifies an optimum number of outliers in a data set. This evaluation of the optimum number can be based on a pre-determined threshold. If the first iteration of the RANSAC algorithm does not identify an optimum number of outliers, another sample can be evaluated using the process described in FIG. 4 to create a model based on another subset of data to identify a greater number of outliers (e.g., better model 320 based on sample 340(2), and if better model 320 is not satisfactory, best model 325 based on sample 340(3), etc.).

Figure 5:
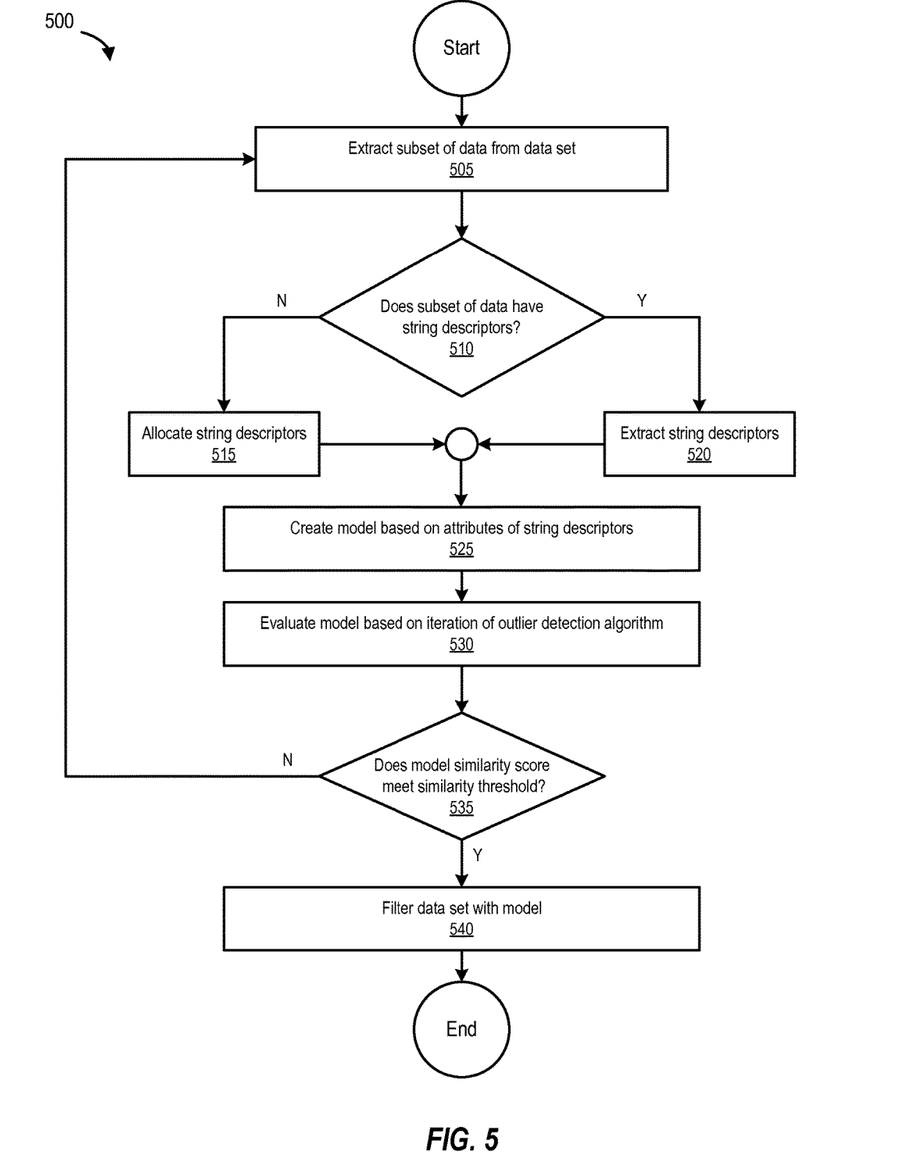
FIG. 5 is a flowchart that illustrates a process for filtering a data set with a model that created based on attributes of string descriptors, according to one embodiment of the present invention.

FIG. 5 is a flowchart that illustrates a process for filtering a data set with a model. The process begins at 505 by extracting a subset of data from a data set. At 510, the process determines whether the subset of data has string descriptors (e.g., string descriptors 240 if the data type is string data). If the subset of data does not have string descriptors, the process, at 515, allocates the string descriptors. If the subset of data has string descriptors, the process, at 520, extracts the string descriptors. At 525, the process creates a model based on the attributes of the string descriptors (e.g., good model 315 based on attributes of string descriptors 240 extracted from sample 340(1) as shown in FIG. 3).

At 530, the process evaluates the model based on an outlier detection algorithm (e.g., an outlier detection process based on the RANSAC algorithm). At 535, the process determines whether the model's similarity score meets (or exceeds) a similarity threshold. For example, if the evaluation of the model using a first iteration of the RANSAC algorithm results in no outliers or very few outliers, a similarity threshold may not be met, and the process extracts another subset of data to create another model. In one example, the similarity threshold may be set by a database administrator based on an expected number of outliers given the size of the database or the number of users actively using the database. In an alternate example, a clustering algorithm can be used to identify filtering thresholds of the subset of data based on the evaluation of the model associated with that subset of data.

Therefore, if the similarity score of the first model (e.g., good model 315) does not meet a similarity threshold (e.g., after the first model is used to evaluate the subset of data and the data set (using the subset of data)), the process repeats the process of FIG. 5 starting at 505 by extracting another subset of data (e.g., sample 340(2)) to create another model (e.g., better model 320) for evaluation by the outlier detection algorithm. In one embodiment, the second model is evaluated using a second iteration of the RANSAC algorithm. However, if even the second model is unsatisfactory (e.g., goes not meet the similarity threshold), the process can extract a third subset of data (e.g., sample 340(3)) to create a third model (e.g., best model 325) for evaluation by a third iteration of the RANSAC algorithm, and so on. The process ends at 540 by filtering the master data set (e.g., data set 80) using the model which identifies meets and/or exceeds the filtering threshold to detect outliers in the data set.

Figure 6:
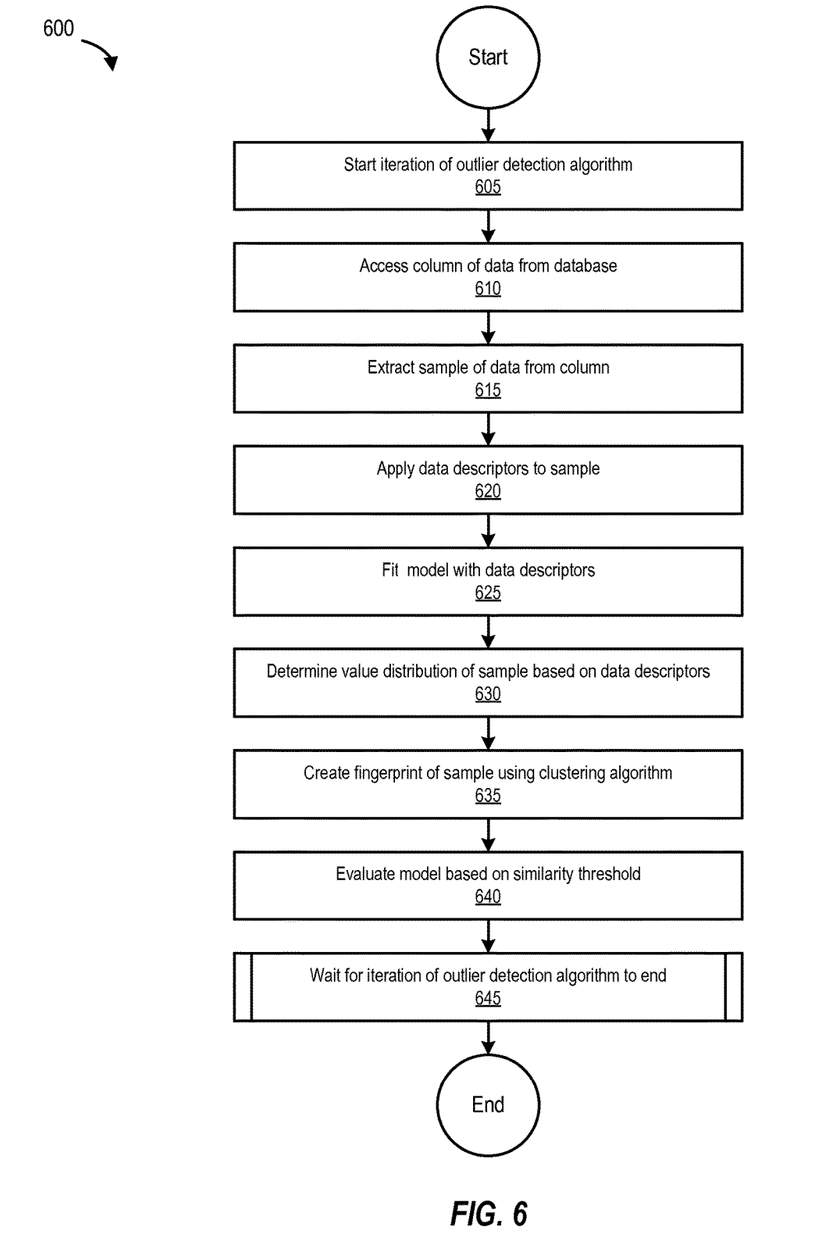
FIG. 6 is a flowchart that illustrates a process for executing an iteration of an outlier detection algorithm, according to one embodiment of the present invention.

FIG. 6 is a flowchart that illustrates a process for evaluating a model created by extracting a sample from a column in a database based on an iteration of an outlier detection algorithm. The process begins at 605 by starting an iteration of an outlier detection algorithm (e.g., the RANSAC algorithm). At 610, the process accesses a column of data in a database (e.g., column 335 in database 330 as shown in FIG. 3). At 615, the process extracts a sample of data from the column (e.g., sample 340 from column 335 as shown in FIG. 3). At 620, the process applies data descriptors to the sample (e.g., string descriptors 240).

At 625, the process fits a model (e.g., a pre-existing model) with the data descriptors (or creates a new model based on the data descriptors). At 630, the process determines a value distribution of the sample based on the data descriptors, and at 635, creates a fingerprint of the sample using a clustering algorithm. At 640, the process evaluates the model based on a similarity threshold (e.g., by using the running iteration of the RANSAC algorithm). The process ends at 645 by waiting for the iteration of the outlier detection algorithm to end.

Figure 7:
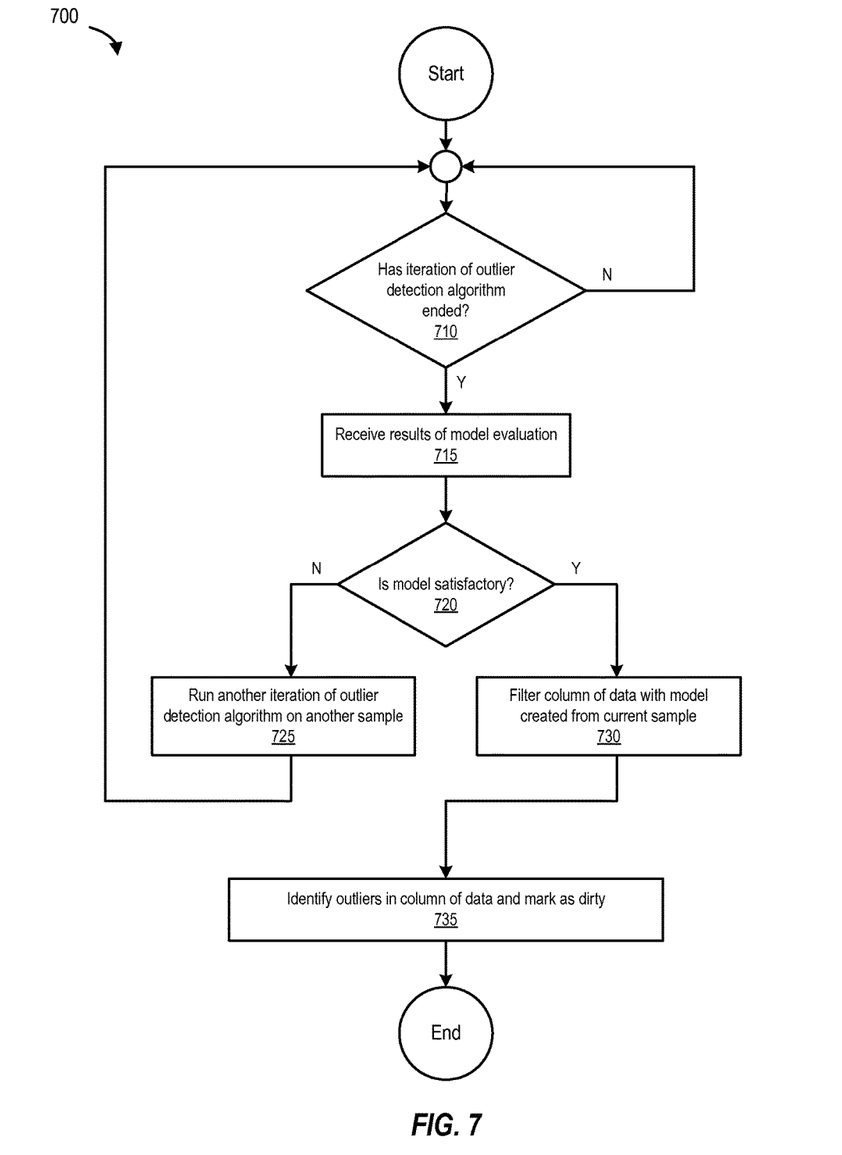
FIG. 7 is a flowchart that illustrates a process for identifying outliers in a data set based on an outlier detection process, according to one embodiment of the present invention.

FIG. 7 is a flowchart that illustrates a process for identifying outliers in a data set based on multiple models and multiple iterations of an outlier detection algorithm. The process begins at 710 by determining if a previous iteration of an outlier detection algorithm has ended. At 715, if the iteration has ended, the process receives the results of the model evaluated by the outlier detection algorithm. At 720, the process determines if the model is satisfactory. For example, and as noted above, if the evaluation of the model using a first iteration of the RANSAC algorithm results in a low similarity score, the process extracts another subset of data to create another model. The determination of whether the model is satisfactory can also be made by a database administrator based on an expected (or anticipated) number of outliers given the size of the database or the number of users actively using the database. For example, if the database is a large database with multiple users modifying data stored in the database, very few or no outliers may indicate that the model is unsatisfactory.

If the model is unsatisfactory, the process, at 725, runs another iteration of the outlier detection algorithm on another sample of data (e.g., sample 340(2) or another subset of data). If the model is deemed satisfactory (e.g., if the results show a high similarity score), the process, at 730, filters the entire column of data with the model created from the current sample of data. The process ends at 735 by identifying outliers in the column and marking the data as "dirty."

Example Computing Environment

Figure 8:
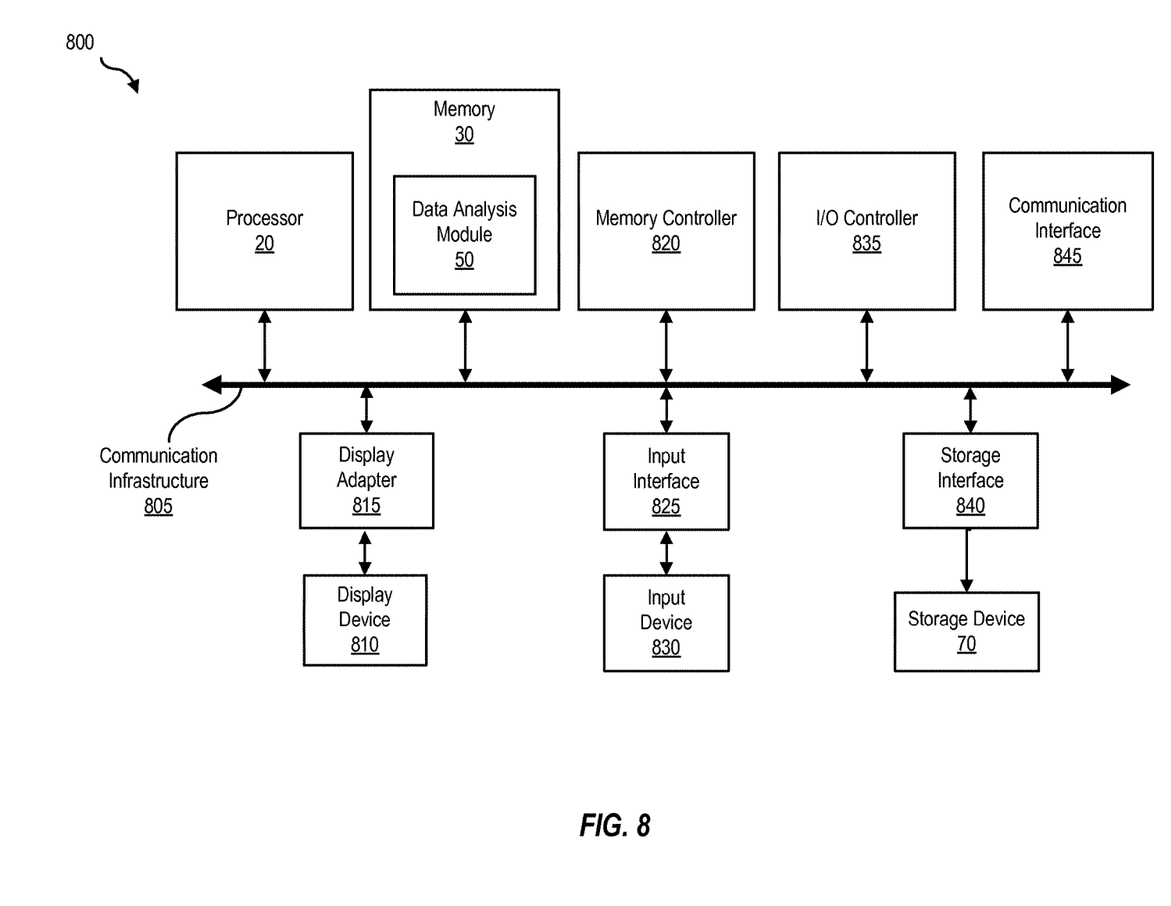
FIG. 8 is a block diagram of a computing system, according to one embodiment of the present invention.

FIG. 8 is a block diagram of a computing system 800 capable of implementing computing device 10 or client 210 as described above. Computing system 800 broadly represents any single or multi-processor computing device or system capable of executing computer-readable instructions. Examples of computing system 800 include, without limitation, any one or more of a variety of devices including workstations, personal computers, laptops, client-side terminals, servers, distributed computing systems, handheld devices (e.g., personal digital assistants and mobile phones), network appliances, storage controllers (e.g., array controllers, tape drive controller, or hard drive controller), and the like. In its most basic configuration, computing system 800 may include at least one processor 20 and a memory 30. By executing the software that implements computing device 10, computing system 800 becomes a special purpose computing device that is configured to perform outlier detection in a database.

Processor 20 generally represents any type or form of processing unit capable of processing data or interpreting and executing instructions. In certain embodiments, processor 20 may receive instructions from a software application or module. These instructions may cause processor 20 to perform the functions of one or more of the embodiments described and/or illustrated herein. For example, processor 20 may perform and/or be a means for performing all or some of the operations described herein. Processor 20 may also perform and/or be a means for performing any other operations, methods, or processes described and/or illustrated herein.

Memory 30 generally represents any type or form of volatile or non-volatile storage device or medium capable of storing data and/or other computer-readable instructions. Examples include, without limitation, random access memory (RAM), read only memory (ROM), flash memory, or any other suitable memory device. Although not required, in certain embodiments computing system 800 may include both a volatile memory unit and a non-volatile storage device. In one example, program instructions implementing a modifiable volume snapshot operation may be loaded into memory 30.

In certain embodiments, computing system 800 may also include one or more components or elements in addition to processor 20 and memory 30. For example, as illustrated in FIG. 8, computing system 800 may include a memory controller 820, an Input/Output (I/O) controller 835, and a communication interface 845, each of which may be interconnected via a communication infrastructure 805. Communication infrastructure 805 generally represents any type or form of infrastructure capable of facilitating communication between one or more components of a computing device. Examples of communication infrastructure 805 include, without limitation, a communication bus (such as an Industry Standard Architecture (ISA), Peripheral Component Interconnect (PCI), PCI express (PCIe), or similar bus) and a network.

Memory controller 820 generally represents any type or form of device capable of handling memory or data or controlling communication between one or more components of computing system 800. For example, in certain embodiments memory controller 820 may control communication between processor 20, memory 30, and I/O controller 835 via communication infrastructure 805. In certain embodiments, memory controller 820 may perform and/or be a means for performing, either alone or in combination with other elements, one or more of the operations or features described and/or illustrated herein.

I/O controller 835 generally represents any type or form of module capable of coordinating and/or controlling the input and output functions of a computing device. For example, in certain embodiments I/O controller 835 may control or facilitate transfer of data between one or more elements of computing system 800, such as processor 20, memory 30, communication interface 845, display adapter 815, input interface 825, and storage interface 840.

Communication interface 845 broadly represents any type or form of communication device or adapter capable of facilitating communication between computing system 800 and one or more additional devices. For example, in certain embodiments communication interface 845 may facilitate communication between computing system 800 and a private or public network including additional computing systems. Examples of communication interface 845 include, without limitation, a wired network interface (such as a network interface card), a wireless network interface (such as a wireless network interface card), a modem, and any other suitable interface. In at least one embodiment, communication interface 845 may provide a direct connection to a remote server via a direct link to a network, such as the Internet. Communication interface 845 may also indirectly provide such a connection through, for example, a local area network (such as an Ethernet network), a personal area network, a telephone or cable network, a cellular telephone connection, a satellite data connection, or any other suitable connection.

In certain embodiments, communication interface 845 may also represent a host adapter configured to facilitate communication between computing system 800 and one or more additional network or storage devices via an external bus or communications channel. Examples of host adapters include, without limitation, Small Computer System Interface (SCSI) host adapters, Universal Serial Bus (USB) host adapters, Institute of Electrical and Electronics Engineers (IEEE) 1394 host adapters, Serial Advanced Technology Attachment (SATA), Serial Attached SCSI (SAS), and external SATA (eSATA) host adapters, Advanced Technology Attachment (ATA) and Parallel ATA (PATA) host adapters, Fibre Channel interface adapters, Ethernet adapters, or the like. Communication interface 845 may also allow computing system 800 to engage in distributed or remote computing. For example, communication interface 845 may receive instructions from a remote device or send instructions to a remote device for execution.

As illustrated in FIG. 8, computing system 800 may also include at least one display device 810 coupled to communication infrastructure 805 via a display adapter 815. Display device 810 generally represents any type or form of device capable of visually displaying information forwarded by display adapter 815. Similarly, display adapter 815 generally represents any type or form of device configured to forward graphics, text, and other data from communication infrastructure 805 (or from a frame buffer, as known in the art) for display on display device 810.

As illustrated in FIG. 8, computing system 800 may also include at least one input device 830 coupled to communication infrastructure 805 via an input interface 825. Input device 830 generally represents any type or form of input device capable of providing input, either computer or human generated, to computing system 800. Examples of input device 830 include, without limitation, a keyboard, a pointing device, a speech recognition device, or any other input device.

As illustrated in FIG. 8, computing system 800 may also include storage device 70 to communication infrastructure 805 via a storage interface 840. Storage device 70 generally represents any type or form of storage devices or mediums capable of storing data and/or other computer-readable instructions. For example, storage device 70 may include a magnetic disk drive (e.g., a so-called hard drive), a floppy disk drive, a magnetic tape drive, an optical disk drive, a flash drive, or the like. Storage interface 840 generally represents any type or form of interface or device for transferring and/or transmitting data between storage device 70, and other components of computing system 800.

In certain embodiments, storage device 70 may be configured to read from and/or write to a removable storage unit configured to store computer software, data, or other computer-readable information. Examples of suitable removable storage units include, without limitation, a floppy disk, a magnetic tape, an optical disk, a flash memory device, or the like. Storage device 70 may also include other similar structures or devices for allowing computer software, data, or other computer-readable instructions to be loaded into computing system 800. For example, storage device 70 may be configured to read and write software, data, or other computer-readable information. Storage device 70 may also be a part of computing system 800 or may be separate devices accessed through other interface systems.

Many other devices or subsystems may be connected to computing system 800. Conversely, all of the components and devices illustrated in FIG. 8 need not be present to practice the embodiments described and/or illustrated herein. The devices and subsystems referenced above may also be interconnected in different ways from that shown in FIG. 8.

Computing system 800 may also employ any number of software, firmware, and/or hardware configurations. For example, one or more of the embodiments disclosed herein may be encoded as a computer program (also referred to as computer software, software applications, computer-readable instructions, or computer control logic) on a computer-readable storage medium. Examples of computer-readable storage media include magnetic-storage media (e.g., hard disk drives and floppy disks), optical-storage media (e.g., CD- or DVD-ROMs), electronic-storage media (e.g., solid-state drives and flash media), and the like. Such computer programs can also be transferred to computing system 800 for storage in memory via a network such as the Internet or upon a carrier medium.

The computer-readable medium containing the computer program may be loaded into computing system 800. All or a portion of the computer program stored on the computer-readable medium may then be stored in memory 30 and/or various portions of storage device 70. When executed by processor 20, a computer program loaded into computing system 800 may cause processor 20 to perform and/or be a means for performing the functions of one or more of the embodiments described and/or illustrated herein. Additionally or alternatively, one or more of the embodiments described and/or illustrated herein may be implemented in firmware and/or hardware. For example, computing system 800 may be configured as an application specific integrated circuit (ASIC) adapted to implement one or more of the embodiments disclosed herein.

Example Networking Environment

Figure 9:
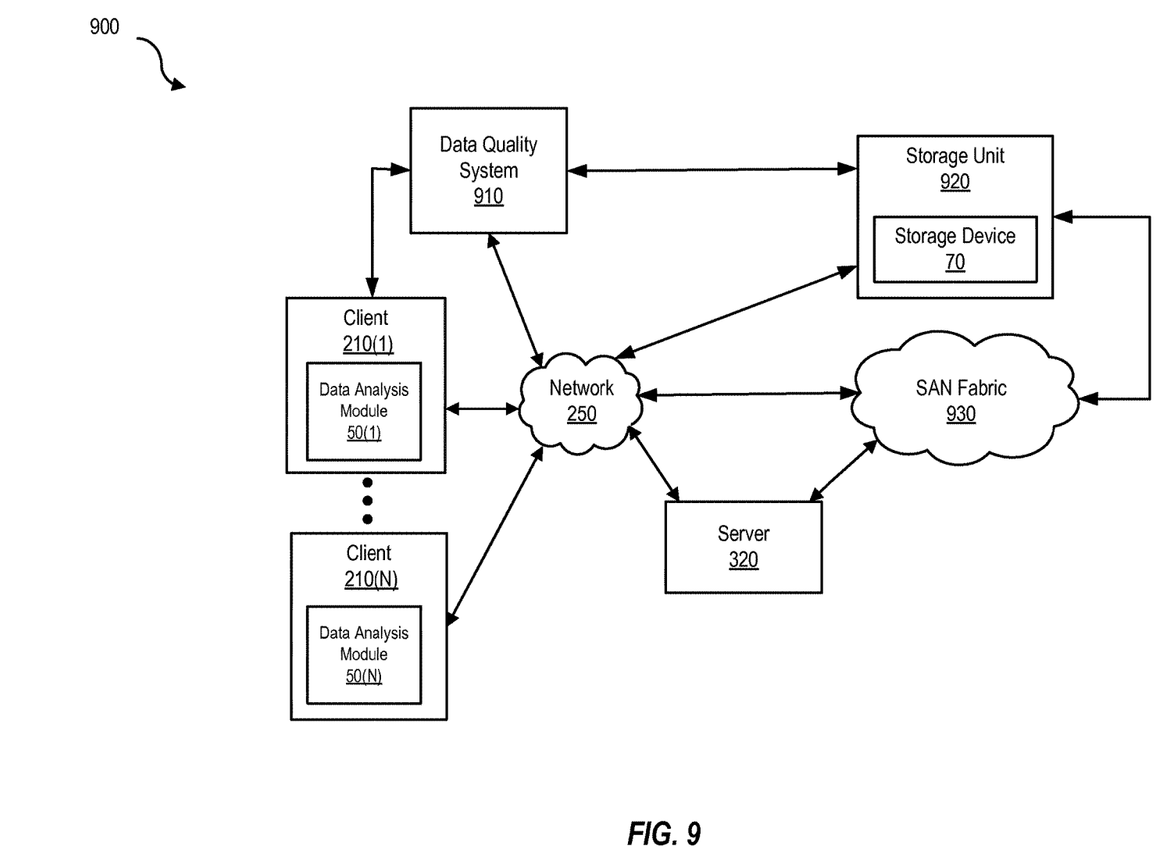
FIG. 9 is a block diagram of a network system, according to one embodiment of the present invention.

FIG. 9 is a block diagram of a network architecture 900 in which computing device 10 may be coupled to network 250. In certain embodiments, network-attached storage (NAS) devices may be configured to communicate with computing device 10 using various protocols, such as Network File System (NFS), Server Message Block (SMB), or Common Internet File System (CIFS).

Network 250 generally represents any type or form of computer network or architecture capable of facilitating communication between multiple computing devices. Network 250 may facilitate communication between computing device 10, client 210, and/or server 310. In certain embodiments, and with reference to computing system 800 of FIG. 8, a communication interface, such as communication interface 845 in FIG. 8, may be used to provide connectivity between computing device 10 and network 250. It should be noted that the embodiments described and/or illustrated herein are not limited to the Internet or any particular network-based environment. For example, network 250 can be a Storage Area Network (SAN).

In at least one embodiment, all or a portion of one or more of the embodiments disclosed herein may be encoded as a computer program and loaded onto and executed by computing device 10, client 210, server 310, or any combination thereof. All or a portion of one or more of the embodiments disclosed herein may also be encoded as a computer program, stored in computing device 10, client 210, or server 310, and distributed over network 250.

In some examples, all or a portion of the computing device in FIG. 1 may represent portions of a cloud-computing or network-based environment. Cloud-computing environments may provide various services and applications via the Internet. These cloud-based services (e.g., software as a service, platform as a service, infrastructure as a service, etc.) may be accessible through a web browser or other remote interface. Various functions described herein may be provided through a remote desktop environment or any other cloud-based computing environment.

In addition, one or more of the components described herein may transform data, physical devices, and/or representations of physical devices from one form to another. For example, a data analysis module 50 may transform behavior of a computing device in order to cause the computing device to perform outlier detection in a database.

Although the present invention has been described in connection with several embodiments, the invention is not intended to be limited to the specific forms set forth herein. On the contrary, it is intended to cover such alternatives, modifications, and equivalents as can be reasonably included within the scope of the invention as defined by the appended claims.

What is claimed is:

1. A method comprising:
   extracting a first subset of data from a data set stored in a database, wherein the data set is a string data set having at least one outlier string data member that reduces the quality of the database storing the string data set;
   creating a first model for the first subset of data using one or more string descriptors describing attributes of string data, wherein the one or more string descriptors are selected from: string length, string character set, co-occurrence of string elements, frequency of string character appearance, entropy of the string data set, similarity of string data, and segmentation of subset of data, the first model being created by:

allocating one or more string descriptors to the first subset of data;

calculating a value distribution of features for one or more allocated string descriptors;

generating a fingerprint for each allocated string descriptor of the first subset of data based on the value distribution, the fingerprint presenting a data distribution feature of an allocated string descriptor; and generating the first model based on the fingerprint;

executing a first iteration of an outlier detection process based on the first model, the first model being evaluated responsive to the first iteration of the outlier detection process to determine whether the first model identifies an optimum number of outliers in the first subset of data, wherein the outlier detection process evaluates the data set based on results of an evaluation of the first subset of data, and the outlier detection process is a multi-iteration Random Sample Consensus (RANSAC) algorithm based on the one or more string descriptors; and responsive to determining that an outlier detection threshold has been met based on the first iteration, identifying the at least one outlier string data member in the string data set based on the executing step; and removing the at least one outlier string data member from the string data set, thereby improving the quality of the database storing the string data set.

2. The method of claim 1, further comprising:

executing a clustering process to identify a first filtering threshold of the first subset of data that is distinct from a similarity threshold and is based on the first model; and filtering the data set based on the first filtering threshold of the first subset of data.

3. The method of claim 2, further comprising:

executing a second iteration of the outlier detection process, wherein executing the second iteration creates a second model and identifies the similarity threshold for a second subset of data that is distinct from the first filtering threshold and is based on the second model, wherein the second subset of data is part of the data set.

4. The method of claim 3, wherein identifying the at least one outlier string data member in the data set further comprises:

comparing the first model of the first subset of data and the second model of the second subset of data, and filtering the data set using a model with the higher similarity threshold, the higher similarity threshold being based on a comparison of the distribution of the one or more string descriptors.

5. The method of claim 2, further comprising:

using the clustering process, creating the fingerprint, the fingerprint associating the first subset of data and the data set based on at least one of the string descriptors.

6. The method of claim 5, further comprising:

determining a value distribution of the string descriptors based on the fingerprint created using the clustering process, and calculating a similarity between the first subset of data and the data set based on the value distribution.

7. The method of claim 1, wherein the data set is part of a database application, and identifying the at least one outlier string data member in the data set further comprises detecting dirty data in the data set that is part of the database application.

8. A computer readable storage medium comprising program instructions executable to:

extract a first subset of data from a data set stored in a database, wherein the data set is a string data set having at least one outlier string data member that reduces the quality of the database storing the string data set;

create a first model for the first subset of data using one or more string descriptors describing attributes of string data, wherein the one or more string descriptors are selected from: string length, string character set, co-occurrence of string elements, frequency of string character appearance, entropy of the string data set, similarity of string data, and segmentation of subset of data, the first model being created by:

allocating one or more string descriptors to the first subset of data;

calculating a value distribution of features for one or more allocated string descriptors;

generating a fingerprint for each allocated string descriptor for the subset of data based on the value distribution, the fingerprint presenting a data distribution feature of an allocated string descriptor; and generating the first model based on the fingerprint;

execute a first iteration of an outlier detection process based on the first model, the first model being evaluated responsive to the first iteration of the outlier detection process to determine whether the first model identifies an optimum number of outliers in the first subset of data, wherein the outlier detection process evaluates the string data set based on results of an evaluation of the first subset of data, and the outlier detection process is a multi-iteration Random Sample Consensus (RANSAC) algorithm based on the one or more string descriptors; and responsive to determining that an outlier detection threshold has been met based on the first iteration, identify the at least one outlier string data member in the string data set based on the executing step; and remove the at least one outlier string data member from the string data set, thereby improving the quality of the database storing the string data set.

9. The computer readable storage medium of claim 8, further comprising:

executing a clustering process to identify a first filtering threshold of the first subset of data that is distinct from a similarity threshold and is based on the first model, filtering the data set based on the first filtering threshold of the first subset of data, and executing a second iteration of the outlier detection process, wherein executing the second iteration creates a second model and identifies the similarity threshold for a second subset of data that is distinct from the first filtering threshold and is based on the second model, wherein the second subset of data is part of the data set.

10. The computer readable storage medium of claim 9, wherein identifying the at least one outlier string data member in the data set further comprises:

comparing the first model of the first subset of data and the second model of the second subset of data, and filtering the data set using a model with the higher similarity threshold, the higher similarity threshold being based on a comparison of the distribution of the one or more string descriptors.

11. The computer readable storage medium of claim 9, further comprising:
using the clustering process, creating the fingerprint, the fingerprint associating the first subset of data and the data set based on at least one of the string descriptors,
determining a value distribution of the string descriptors based on the fingerprint created using the clustering process, and
calculating a similarity between the first subset of data and the data set based on the value distribution.

12. The computer readable storage medium of claim 8, wherein the data set is part of a database application, and identifying the at least one outlier string data member in the data set further comprises detecting dirty data in the data set that is part of the database application.

13. A system comprising:
one or more processors; and
a memory coupled to the one or more processors, wherein the memory stores program instructions executable by the one or more processors to:
extract a first subset of data from a data set stored in a database, wherein the data set is a string data set having at least one outlier string data member that reduces the quality of the database storing the string data set;
create a first model for the first subset of data using one or more string descriptors describing attributes of string data, wherein the one or more string descriptors are selected from: string length, string character set, co-occurrence of string elements, frequency of string character appearance, entropy of the string data set, similarity of string data, and segmentation of subset of data, the first model being created by:
allocating one or more string descriptors to the first subset of data;
calculating a value distribution of features for one or more allocated string descriptors;
generating a fingerprint for each allocated string descriptor for the subset of data based on the value distribution, the fingerprint presenting a data distribution feature of an allocated string descriptor; and
generating the first model based on the fingerprint;
execute a first iteration of an outlier detection process based on the first model, the first model being evaluated responsive to the first iteration of the outlier detection process to determine whether the first model identifies an optimum number of outliers in the first subset of data, wherein
the outlier detection process evaluates the string data set based on results of an evaluation of the first subset of data, and
the outlier detection process is a multi-iteration Random Sample Consensus (RANSAC) algorithm based on the one or more string descriptors; and
responsive to determining that an outlier detection threshold has been met based on the first iteration, identify the at least one outlier string data member in the string data set based on the executing step; and
remove the at least one outlier string data member from the string data set, thereby improving the quality of the database storing the string data set.

14. The system of claim 13, further comprising:
executing a clustering process to identify a first filtering threshold of the first subset of data that is distinct from a similarity threshold and is based on the first model,
filtering the data set based on the first filtering threshold of the first subset of data, and
executing a second iteration of the outlier detection process, wherein executing the second iteration creates a second model and identifies the similarity threshold for a second subset of data that is distinct from the first filtering threshold and is based on the second model, wherein the second subset of data is part of the data set.

15. The system of claim 14, wherein identifying the at least one outlier string data member in the data set further comprises:
comparing the first model of the first subset of data and the second model of the second subset of data, and
filtering the data set using a model with the higher similarity threshold, the higher similarity threshold being based on a comparison of the distribution of the one or more string descriptors.

* * * * *